US009320471B2

(12) United States Patent
Hayes et al.

(10) Patent No.: US 9,320,471 B2
(45) Date of Patent: Apr. 26, 2016

(54) ALGORITHM SENSOR AUGMENTED BOLUS ESTIMATOR FOR SEMI-CLOSED LOOP INFUSION SYSTEM

(75) Inventors: Andrew C. Hayes, Simi Valley, CA (US); John J. Mastrototaro, Los Angeles, CA (US); Sheldon B. Moberg, Thousand Oaks, CA (US); John C. Mueller, Jr., Simi Valley, CA (US); H. Bud Clark, Chatsworth, CA (US); Mike Charles Vallet Tolle, Van Nuys, CA (US); Gary L. Williams, Gardena, CA (US); Bihong Wu, Oak Park, CA (US); Garry M. Steil, Pasadena, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 820 days.

(21) Appl. No.: 13/529,278

(22) Filed: Jun. 21, 2012

(65) Prior Publication Data

US 2012/0259278 A1 Oct. 11, 2012

Related U.S. Application Data

(60) Continuation of application No. 12/436,308, filed on May 6, 2009, now Pat. No. 8,226,556, which is a division of application No. 11/322,489, filed on Dec. 30, 2005, now Pat. No. 7,547,281.

(60) Provisional application No. 60/649,936, filed on Feb. 1, 2005.

(51) Int. Cl.
*A61B 5/145* (2006.01)
*A61M 5/172* (2006.01)
(Continued)

(52) U.S. Cl.
CPC ........... *A61B 5/7239* (2013.01); *A61B 5/14532* (2013.01); *A61M 5/1723* (2013.01);
(Continued)

(58) Field of Classification Search
CPC ................. A61M 2230/201; A61M 2230/005; A61M 2005/14208; A61M 2205/18; A61M 2205/35; A61M 5/1723; A61B 5/14532; A61B 5/7239; A61B 5/14503; A61B 5/1468; A61B 5/1473; A61B 5/1486; A61B 5/14865; G06F 19/3406; G06F 19/3437; G06F 19/3468
USPC ........................ 600/309, 345–366; 604/65, 66
See application file for complete search history.

(56) References Cited

U.S. PATENT DOCUMENTS 3,621,357 A 11/1971 Kubo et al.
3,826,887 A 7/1974 Pemberton
(Continued)

FOREIGN PATENT DOCUMENTS

WO 03/006091 A1 1/2003
WO 2004/060455 A1 7/2004

OTHER PUBLICATIONS

PCT International Search Report and Written Opinion for Application No. PCT/US2006/003350.
(Continued)

*Primary Examiner* — Navin Natnithithadha
(74) *Attorney, Agent, or Firm* — Medtronic MiniMed, Inc.

(57) ABSTRACT

An infusion system is for infusing a fluid into the body of a patient. The infusion system includes at least one sensor for monitoring blood glucose concentration of the patient and an infusion device for delivering fluid to the patient. The sensor produces at least one sensor signal input. The infusion device uses the at least one sensor signal input and a derivative predicted algorithm to determine future blood glucose levels. The infusion device delivers fluid to the patient when future blood glucose levels are in a patient's target range. The infusion device is capable of suspending and resuming fluid delivery based on future blood glucose levels and a patient's low shutoff threshold. The infusion device suspends fluid delivery when future blood glucose levels falls below the low shutoff threshold. The infusion device resumes fluid delivery when a future blood glucose level is above the low shutoff threshold.

8 Claims, 15 Drawing Sheets

(51) Int. Cl.
*A61B 5/00* (2006.01)
*A61M 5/142* (2006.01)
*G06F 19/00* (2011.01)

(52) U.S. Cl.
CPC .. *G06F19/3468* (2013.01); *A61M 2005/14208* (2013.01); *A61M 2205/18* (2013.01); *A61M 2205/35* (2013.01); *A61M 2230/201* (2013.01); *G06F 19/3406* (2013.01); *G06F 19/3437* (2013.01)

(56) References Cited

U.S. PATENT DOCUMENTS

| | | | |
|---|---|---|---|
| 3,834,617 | A | 9/1974 | Dyntar |
| 3,986,571 | A | 10/1976 | Strobel et al. |
| 4,291,692 | A | 9/1981 | Bowman et al. |
| 4,475,901 | A | 10/1984 | Kraegen et al. |
| 4,786,394 | A | 11/1988 | Enzer et al. |
| 5,050,612 | A | 9/1991 | Matsumura |
| 5,068,536 | A | 11/1991 | Rosenthal |
| 5,497,772 | A | 3/1996 | Schulman et al. |
| 5,507,288 | A | 4/1996 | Bocker et al. |
| 5,569,186 | A | 10/1996 | Lord et al. |
| 5,665,065 | A | 9/1997 | Colman et al. |
| 5,695,464 | A | 12/1997 | Viallet |
| 5,813,403 | A | 9/1998 | Soller et al. |
| 5,822,715 | A | 10/1998 | Worthington et al. |
| 5,830,133 | A | 11/1998 | Osten et al. |
| 5,885,211 | A | 3/1999 | Eppstein et al. |
| 6,049,727 | A | 4/2000 | Crothall |
| 6,064,896 | A | 5/2000 | Rosenthal |
| 6,088,608 | A | 7/2000 | Schulman et al. |
| 6,175,752 | B1 | 1/2001 | Say et al. |
| 6,272,364 | B1 | 8/2001 | Kurnik |
| 6,379,301 | B1 | 4/2002 | Worthington et al. |
| 6,416,293 | B1 | 7/2002 | Bouchard et al. |
| 6,424,873 | B1 | 7/2002 | Przybylski |
| 6,541,266 | B2 | 4/2003 | Modzelewski et al. |
| 6,544,212 | B2 | 4/2003 | Galley et al. |
| 6,546,269 | B1 | 4/2003 | Kurnik |
| 6,551,276 | B1 | 4/2003 | Mann et al. |
| 6,554,798 | B1 | 4/2003 | Mann et al. |
| 6,558,351 | B1 | 5/2003 | Steil et al. |
| 6,561,978 | B1 | 5/2003 | Conn et al. |
| 6,572,542 | B1 | 6/2003 | Houben et al. |
| 6,579,690 | B1 | 6/2003 | Bonnecaze et al. |
| 6,931,327 | B2 | 8/2005 | Goode, Jr. et al. |
| 7,011,630 | B2 | 3/2006 | Desai et al. |
| 7,022,072 | B2 | 4/2006 | Fox et al. |
| 7,060,059 | B2 | 6/2006 | Keith et al. |
| 7,267,665 | B2 | 9/2007 | Steil et al. |
| 7,276,029 | B2 | 10/2007 | Goode, Jr. et al. |
| 7,299,080 | B2 | 11/2007 | Acosta et al. |
| 7,354,420 | B2 | 4/2008 | Steil et al. |
| 7,402,153 | B2 | 7/2008 | Steil et al. |
| 7,436,511 | B2 | 10/2008 | Ruchti et al. |
| 7,519,408 | B2 | 4/2009 | Rasdal et al. |
| 7,547,281 | B2 | 6/2009 | Hayes et al. |
| 7,583,990 | B2 | 9/2009 | Goode, Jr. et al. |
| 7,599,726 | B2 | 10/2009 | Goode, Jr. et al. |
| 7,766,830 | B2 | 8/2010 | Fox et al. |
| 7,878,975 | B2 | 2/2011 | Liljeryd et al. |
| 2002/0146835 | A1 | 10/2002 | Modzelewski et al. |
| 2003/0060753 | A1 | 3/2003 | Starkweather et al. |
| 2003/0130616 | A1 | 7/2003 | Steil et al. |
| 2005/0010090 | A1 | 1/2005 | Acosta et al. |
| 2005/0020892 | A1 | 1/2005 | Acosta et al. |
| 2007/0060803 | A1 | 3/2007 | Liljeryd et al. |
| 2007/0282180 | A1 | 12/2007 | Caduff et al. |

OTHER PUBLICATIONS

PCT International Preliminary Report on Patentability for Application No. PCT/US2006/003350.
Doran C V et al, "Derivative weighted active insulin control modelling and clinical trials for ICU patients", Aug. 16, 2004, pp. 855-866, vol. 26, No. 10, Dec. 2004, Christchurch, New Zealand.

ALGORITHM SENSOR AUGMENTED BOLUS ESTIMATOR FOR SEMI-CLOSED LOOP INFUSION SYSTEM

RELATED APPLICATIONS

This application is a continuation application of U.S. patent application Ser. No. 12/436,308, filed May 6, 2009, which is a divisional application of U.S. patent application Ser. No. 11/322,489, filed Dec. 30, 2005, now U.S. Pat. No. 7,547,281, which claims the benefit of prior filed U.S. Provisional Application Ser. No. 60/649,936, filed on Feb. 1, 2005.

FIELD OF THE INVENTION

Embodiments of the present invention relate to semi-closed loop drug delivery systems, and more specifically to systems for controlling the infusion rate of insulin, based on continuously monitored body glucose levels.

BACKGROUND OF THE INVENTION

The pancreas of a normal healthy person produces and releases insulin into the blood stream in response to elevated blood plasma glucose levels. Beta cells (β-cells), which reside in the pancreas, produce and secrete the insulin into the blood stream, as it is needed. When β-cells become incapacitated or die, a condition known as Type I diabetes mellitus results (or in some cases when β-cells produce insufficient quantities of insulin, Type II diabetes results), then insulin must be provided to the body from another source.

Traditionally, since insulin cannot be taken orally, insulin has been injected with a syringe. More recently, use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. As of 1995, less than 5% of Type I diabetics in the United States were using infusion pump therapy. Presently over 12% of the more than 900,000 Type I diabetics in the U.S. are using infusion pump therapy. And the percentage of Type I diabetics that use an infusion pump is growing at an absolute rate of over 2% each year. Moreover, the number of Type I diabetics is growing at 3% or more per year. In addition, growing numbers of insulin using Type II diabetics are also using infusion pumps.

SUMMARY OF THE DISCLOSURE

According to an embodiment of the invention, an infusion system is for infusing a fluid into the body of a patient. In particular embodiments, the infusion system includes at least one sensor for monitoring blood glucose concentration of the patient and an infusion device for delivering fluid to the patient. In further embodiments, the sensor produces at least one sensor signal input. In additional particular embodiments, the infusion device uses the at least one sensor signal input and a derivative predicted algorithm to determine future blood glucose levels. In some embodiments, the infusion device delivers fluid to the patient when future blood glucose levels are in a patient's predefined target range. In other embodiments, the infusion device is capable of suspending and resuming fluid delivery based on future blood glucose levels and a patient's predefined low shutoff threshold. In still further embodiments, the infusion device suspends fluid delivery when a future blood glucose level falls below the predefined low shutoff threshold. In additional embodiments, the infusion device resumes fluid delivery when a future blood glucose level is above the predefined low shutoff threshold.

In some embodiments, the predefined low shutoff threshold is always above the infusion system's lowest shutoff threshold. In still further embodiments the infused fluid is insulin and the infusion system includes alarm based capabilities to provide alerts to the patient. In some embodiments, the patient selects at least one alarm to activate, and the at least one alarm includes an audible alarm for providing audible alerts, a vibration alarm for providing tactile alert, and a visual alarm for providing visual alerts.

According to another embodiment of the invention, an infusion system is for infusing a fluid into the body of a patient. The infusion system includes a sensor system that includes a sensor for monitoring blood glucose concentration of a patient, and produces at least one sensor signal, which is representative of the blood glucose concentration of the patient. In particular embodiments, the at least one sensor signal is used to generate at least one sensor signal input. In particular embodiments, the infusion system also includes a controller, which uses the at least one sensor signal input to determine at least one sensor-derived blood glucose trend. In other embodiments, the at least one sensor-derived blood glucose trend is used to determine blood glucose levels at a predetermined time in the future. In still further particular embodiments, the infusion system also includes a delivery system that infuses a fluid into the patient. In some embodiments, operation of the delivery system is affected by commands from the controller and the patient and, in other embodiments, the controller suspends fluid delivery if the at least one sensor-derived trend yields at least one blood glucose level reading that is below a predefined low shutoff threshold. In particular embodiments, the controller resumes delivery of the fluid when the at least one sensor-derived trend yields at least one blood glucose level reading that is above the predefined low shutoff threshold. In other embodiments, the predefined low shutoff threshold is always above the infusion system's lowest shutoff threshold. In other additional embodiments, the controller uses a derivative predicted algorithm to determine the at least one sensor-derived blood glucose trend. In some embodiments, the infused fluid is insulin. In particular embodiments, the infusion system also includes an alarm to provide alerts to the patient. In additional embodiments, the patient selects at least one alarm to activate. In other embodiments, the at least one alarm includes an audible alarm for providing audible alerts, a vibration alarm for providing tactile alert, and a visual alarm for providing visual alerts.

According to another embodiment of the invention, a method is for predicting blood glucose concentration of a patient. In particular embodiments, the method first measures current blood glucose concentration using a sensor. In other embodiments, the sensor yields at least one sensor signal input which is representative of the current blood glucose concentration. In additional embodiments, the method inputs the at least one sensor signal input to a derivative predicted algorithm. In other embodiments, the method determines the future blood glucose concentration using the derivative predicted algorithm.

BRIEF DESCRIPTION OF THE DRAWINGS

A detailed description of embodiments of the invention will be made with reference to the accompanying drawings, where like numerals designate corresponding parts or cross-sections in the several figures.

DETAILED DESCRIPTION OF THE PREFERRED EMBODIMENTS

The present invention is embodied in a semi-closed loop infusion system for assisting in the regulation of the rate of fluid infused into a body of a patient, based on feedback from an analyte concentration measurement taken from the body using a sensor, in addition to patient programming. In particular embodiments, an improved algorithm may be used that suggests infusion dosage, or bolus amounts, based on particular trends of sensor-derived body characteristics. For example, in the case of diabetic patients, when sensor-derived blood glucose levels are trending down, the semi-closed loop algorithm may recommend less insulin intake. If sensor-derived blood glucose levels are trending up, the system may recommend more insulin intake. Examples of different bolus types and how to program and/or deliver a bolus can be found in U.S. Pat. No. 6,554,798 issued on Apr. 29, 2003 to Mann et al., and entitled "External Infusion Device with Remote Programming, Bolus Estimator and/or Vibration Alarm Capabilities", which is specifically incorporated by reference herein. In some embodiments, the algorithms may be employed in semi-closed loop infusion systems, while, in other embodiments; the algorithms are utilized in closed-loop infusion systems.

Figure 15:
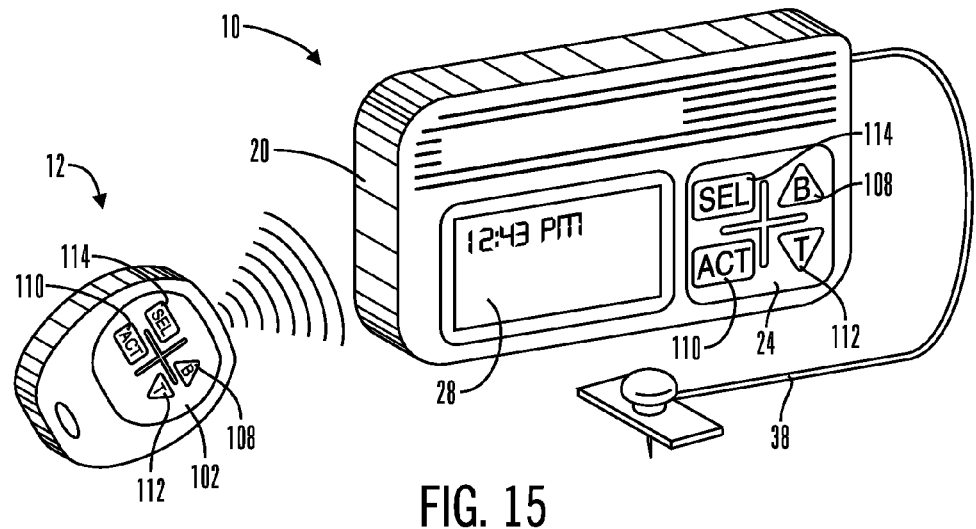
FIG. 15 is a perspective view of an embodiment of an infusion device in accordance with an embodiment of the present invention.
Figure 16:
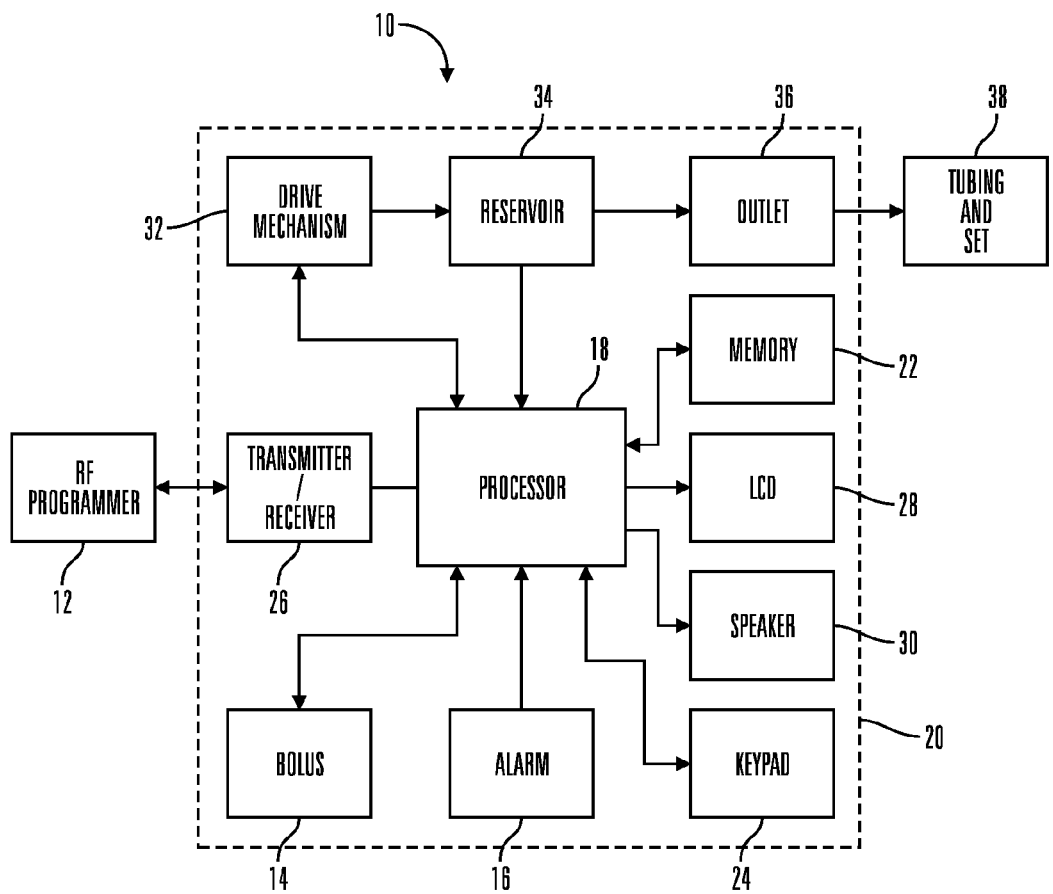
FIG. 16 is a simplified schematic view of the embodiment of FIG. 15.

Embodiments of the invention may be employed in various infusion environments including, but not limited to a biological implant environment. Other environments include, but are not limited to external infusion devices, pumps, or the like. Fluids that may be infused include, but are not limited to insulin formulations and other formulations having other pharmacological properties. As illustrated in FIGS. 15 and 16, embodiments of an external infusion device 10 may include an optional remote RF programmer 12, a bolus capability 14 and/or an alarm 16. The RF programmer 12 and bolus capability 14 communicate with a processor (controller) 18 contained in a housing 20 of the external infusion device 10. The processor (controller) 18 is used to run programs and control the external infusion device 10, and is connected to an internal memory device 22 that stores programs, historical data, user defined information and parameters. In particular embodiments, the memory device is a Flash memory and SRAM; however, in alternative embodiments, the memory device 22 may include other memory storage devices such as ROM, DRAM, RAM, EPROM, dynamic storage such as other flash memory, energy efficient hard-drive, or the like. In other embodiments, the external infusion device 10 is an external infusion pump that is programmed through a keypad 24 on the housing 20 or by commands received from the RF programmer 12 through a transmitter/receiver 26. Feedback from the external infusion device 10 on status or programming changes are displayed on an LCD 28 and/or audibly through a speaker 30. In alternative embodiments, the keypad 24 may be omitted and the LCD 28 may be used as a touch screen input device or the keypad 24 may utilize more keys or different key arrangements then those illustrated in the figures. The processor (controller) 18 is also coupled to a drive mechanism 32 that is connected to a fluid reservoir 34 containing fluid that is expelled through an outlet 36 in the reservoir 34 and housing 20, and then into a body of a user through tubing and a set 38. In further alternative embodiments, the keypad 24, LCD 20, speaker 24 may be omitted from the external infusion device, and all programming and data transfer is handled through the RF programmer 12.

Generally, in particular embodiments the external infusion device 10 is an external insulin pump having the capability to deliver 0 to 35 Units/hour in basal rates and up to 25.0 Units per meal bolus of U-100 Insulin. In alternative embodiments, the external pump delivers other concentrations of insulin, or other fluids, and may use other limits on the delivery rate.

To deliver a bolus with the keypad the user uses the keypad 24 and keys 108, 110, 112 and/or 114 to can program and/or deliver one or more bolus types through a single touch key or by the use of one or more menus. In alternative embodiments, the user can program and/or deliver a bolus with the optional RF programmer 12.

The infusion system infuses a fluid, such as medication, chemicals, enzymes, antigens, hormones, vitamins or the like, into a body of a user. In particular embodiments of the present invention, the infusion system is an external infusion pump, which includes an RF programming capability, a carbohydrate (or bolus) estimation capability and/or vibration alarm capability. Particular embodiments are directed towards use in humans; however, in alternative embodiments, the external infusion devices may be used in animals.

The sensor included in the infusion system may be implanted in and/or through subcutaneous, dermal, sub-dermal, inter-peritoneal or peritoneal tissue. In other embodiments of the present invention, the sensor and monitor are for determining glucose levels in the blood and/or body fluids of the user without the use of, or necessity of, a wire or cable connection between the transmitter and the monitor. However, it will be recognized that further embodiments of the invention may be used to determine the levels of other agents, characteristics or compositions, such as hormones, cholesterol, medication concentrations, pH, oxygen saturation, viral loads (e.g., HIV), or the like. In other embodiments, the sensor may also include the capability to be programmed or calibrated using data received by a telemetered characteristic monitor transmitter device, or may be calibrated at the monitor device (or receiver). The telemetered characteristic monitor system is primarily adapted for use in subcutaneous human tissue. However, still further embodiments may be placed in other types of tissue, such as muscle, lymph, organ tissue, veins, arteries or the like, and used in animal tissue. Embodiments may provide sensor readings on an intermittent or continuous basis.

In particular embodiments, bolus estimation algorithms render bolus recommendations based upon various parameters including, but not limited to meal content, blood glucose concentrations, blood glucose concentration time rate of change, insulin-on-board, insulin duration factor, target blood glucose, insulin sensitivity and the like. In some embodiments, these various parameters may be inputted by the patient, automatically provided to the processor (controller) by a sensor, downloaded from a remote computer, or the like.

In specific embodiments, a bolus estimation algorithm renders bolus recommendations based upon meal content (user input), blood glucose concentration BG (user or meter input), and blood glucose concentration time rate of change (derived from data furnished by a continuous glucose monitoring system). The meal content may be calculated by the patient and inputted directly into the infusion device. In other embodiments, the meal content may be downloaded from a remote computer containing a food library or the like. In additional embodiments, the patient's blood glucose concentration may be directly inputted to the processor (controller) by a glucose meter with or without patient interaction. In still further embodiments, the patient's BG concentration rate of change may be received by the processor (controller) directly from an external and/or implantable continuous glucose monitoring system of the type described in U.S. Pat. No. 5,741,211 issued on Apr. 21, 1998 to Renirie, et al., and entitled "System and method for continuous monitoring of diabetes-related blood constituents", which is specifically incorporated by reference herein. Sensor estimated glucose concentration, or SG, may be determined by a calibrated glucose sensor system of the present embodiment.

In further embodiments, the infusion device may be capable of receiving data from various linked devices including, but not limited to a continuous glucose monitoring system, a glucose meter, a remote computer, and the like. In some embodiments, the infusion device may receive data in five-minute intervals from any one or more of the linked devices. In further embodiments, the receive-time may range from 1 to 10 minutes. In other embodiments, data may be received in 20, 30, 40, 50 or 60 minute intervals.

In particular embodiments, a derivative predicted algorithm is utilized by the infusion device to compute proportional blood glucose correction when measured blood glucose values are outside of a patient's target range. In further embodiments, the derivative predicted algorithm may also make correction adjustments for insulin-on-board values and/or compute food corrections. The derivative predicted algorithm utilizes BG information gathered from the patient, glucose monitor, glucose meter, continuous glucose monitoring system or the like. In particular embodiments, the processor (controller) employing the derivative predicted algorithm receives data from a continuous and/or near continuous glucose monitoring system where measurements are taken over a specified period of time.

In some embodiments, sensor-derived blood glucose levels are based on trends yielding a prediction of blood glucose levels at a given number of minutes into the future. The future BG values are obtained (and/or predicted) by using the derivative of the current BG value as described by the derivative predicted algorithm. In the following embodiments, these blood glucose levels are termed "derivative corrected" blood glucose levels. To determine the derivative corrected blood glucose, various algorithms may be employed utilizing patient-defined parameters, sensor readings, infusion device defined parameters, and the like. In particular embodiments, certain algorithms accept continuous glucose sensor input and use the blood glucose data to make correction adjustments based upon the derivative of sensor derived blood glucose values.

In some embodiments, various parameters may be used by the algorithm to calculate the derivative predicted BG values. In particular embodiments, the algorithm may utilize parameters inputted by the patient and/or default parameters stored in the processor (controller). Patient defined parameters may include, but are not limited to, current blood glucose concentrations (BG), meal carbohydrate content (CHO), sensor current sample at time period n (Isig(n)) (obtained from a continuous glucose sensor), system calibration factor (CF) (obtained from a continuous glucose monitoring system), insulin-on-board at time period n (IOB(n)) and the like. IOB(n) is a state variable maintained by the processor (controller) of the infusion device. In some embodiments, this value may also be referred to as active insulin, or Ia(n). In still further embodiments, additional parameters may be inputted to the infusion device by the patient including insulin sensitivity, insulin duration factor and the like. In still further embodiments, fewer parameters may be utilized.

In additional particular embodiments, default parameters stored in the infusion device may include, but are not limited to, maximum (high) BG value of the patient's target range (BGh), minimum (low) BG value of the patient's target range (BGl), sensor glucose rate factor (Td), insulin sensitivity factor (ISF), carbohydrate sensitivity factor (CSF) and the like. In some embodiments, these values may be preset in the infusion device and not user adjustable. In further embodiments, the patient may adjust BGh, BGl, ISF, and/or CSF. In specific embodiments, the sensor glucose rate factor Td is not user adjustable. A nominal value of 15 minutes may be factory preset. In still further embodiments, the doctor, healthcare professional and/or patient may toggle Td between its nominal value and 0.

In particular embodiments, the derivate predicted algorithm may output variables including a total correction recommended value (Tc), and/or a proportional correction portion of the total correction recommendation (Pc). The total correction recommended Tc is the amount reported to the patient as the bolus recommendation. The proportional correction portion is equal to Tc minus the food correction. In some embodiments Pc will not be reported to the patient. In other embodiments, Pc may be used in additional algorithms employed by the infusion device for delivering a particular type of bolus (i.e., dual wave bolus algorithm, square wave bolus algorithm, presentation of details algorithm, and the like).

In specific embodiments, the derivative predicted algorithm may calculate the first derivative of the sensor current sample at time period n (dIsig(n)). The first derivative dIsig(n)

may be calculated from the slope of Isig(n) versus time over the previous 30 minutes using a Savitzky-Golay finite impulse response filter. Using a sampling interval of 5 minutes, the filter coefficients that will provide the derivative are listed in Table A:

TABLE A

Order 7 Savitzky-Golay derivative filter coefficients for 5 minute sampling frequency

| $a_0$ | $a_1$ | $a_2$ | $a_3$ | $a_4$ | $a_5$ | $a_6$ |
|---|---|---|---|---|---|---|
| 3/140 | 2/140 | 1/140 | 0 | −1/140 | −2/140 | −3/140 | dIsig(n) is then given by the following equation:

$$dIsig(n) = \sum_{i=0}^{6} a_i \cdot Isig(n-i)$$

Missing samples, whether unavailable due to transmission errors or discarded by sensor system integrity checks may be replaced with the preceding value. When the first valid Isig sample is acquired following an initialization period or period where the sensor signal has been invalid for more than 6 samples, the Isig (n−1) through Isig (n−6) will be replaced with Isig(n) (i.e., filter initialization).

The algorithm may next calculate the first derivative of sensor glucose SG at the most recent sample yielding dSG(n):

$dSG(n)=CF \cdot dIsig(n)$

When the derivative correction algorithm is utilized by the infusion device, the previous calculations allow the algorithm to provide the processor (controller) with the "derivative predicted" blood glucose value (BGc). After BGc has been initialized to BG, the equation is:

$BGc=BG+Td \cdot dSG(n)$

BGc describes the predicted BG value a specific amount of time into the future. In some embodiments, the derivative predicted algorithm may be disabled and correction insulin may be determined based on traditional algorithms employed by infusion device systems where BGc would simply equal BG. Additionally, if the derivative of sensor glucose, or dSG is zero, the algorithm reverts back to a more traditional correction algorithm employed by infusion devices as described in U.S. Pat. No. 6,554,798 issued on Apr. 29, 2003 to Mann et al., and entitled "External Infusion Device with Remote Programming, Bolus Estimator and/or Vibration Alarm Capabilities."

The proportional correction (Pc), may be calculated using the following equations:
Initialize Pc to zero Pc=0,
High BG Proportional Correction:
If BG is input, and BGc>BGh, then Pc=(BGc−BGh)/ISF
Adjustment of high BG proportional correction with insulin on-board:
If Pc>IOB(n), then Pc=Pc−IOB(n)
Otherwise, set Pc=0
Low BG Proportional Correction:
If BG is input and BGc<BGl, then Pc=(BGc−BGl)/ISF
In some embodiments, low BG proportional correction will always be negative and is never adjusted with insulin on board. Pc will equal to zero when BG is not entered or when BGc is within the patient's target range as defined by the infusion device.

In further embodiments, the algorithm may also calculate the food correction (Fc), by first initializing Fc to zero: Fc=0
If CHO is input, then Fc=CHO/ISF
Note: Fc=0 when CHO is not entered
In particular embodiments, the final corrections returned by the algorithm are Tc and Pc. The total correction is given by:

$Tc=Fc+Pc$

If Tc<0, then Tc=0
If Pc<0, then Pc=0
The negative amount from a low BG proportional correction of sufficiently great magnitude may completely cancel out the positive amount from a food correction. In some embodiments, the derivative predicted algorithm always returns non-negative values for Tc and Pc, imposing a floor of zero for each.

In comparison to insulin delivery algorithms utilized in traditional infusion devices (for example the MiniMed Paradigm® 515 Infusion Pump), embodiments of the present invention attempt to automate the process by requiring less patient interaction. In particular embodiments, 3-dimensional figures (FIGS. 1-6) are used to evaluate performance of the derivative predicted algorithm versus that of a traditional infusion device. The x-y plane of the plots denotes the values of the variables BG and CHO furnished to each algorithm. The z-axis denotes the total insulin bolus correction (Tc) recommended by each algorithm. For each bolus recommendation made, a vertical column is plotted at the x-y coordinates corresponded to the pair of BG and CHO values used. The height of the vertical column is equal to the bolus recommendation corresponding to those values of BG and CHO. Taken together, the vertical columns of the plot define the recommendation envelope for the algorithm of interest. Sixteen values of BG (mg/dl, range=[50,100]), and eleven values of CHO (grams, range=[0,100]) were used to create each recommendation envelope. BG and CHO are varied within each plot, but all other parameters remain constant. Two values of IOB (U, IOB=0 or 2) and three values of dSG (mg/dl per min, dSG=0, −2, or +2), were used to create six recommendation envelopes for each algorithm. Fixed values were chosen for ISF, CSF, and the Target range (BGh and BGl). The values chosen were reasonable in terms of the typical ranges for Type I Diabetics. Each of the plots, FIGS. 1-6 compare traditional infusion device algorithms with embodiments of the present invention utilizing derivative predicted algorithms. They include three plots having the first plot show the recommendation envelope of a traditional infusion device using traditional infusion delivery algorithms. The second plot within each figure shows the recommendation envelope of an infusion device utilizing derivative predicted algorithms. And the final plot of each figure shows the difference between the two algorithms at every point on their recommendation envelopes.

Figure 1:
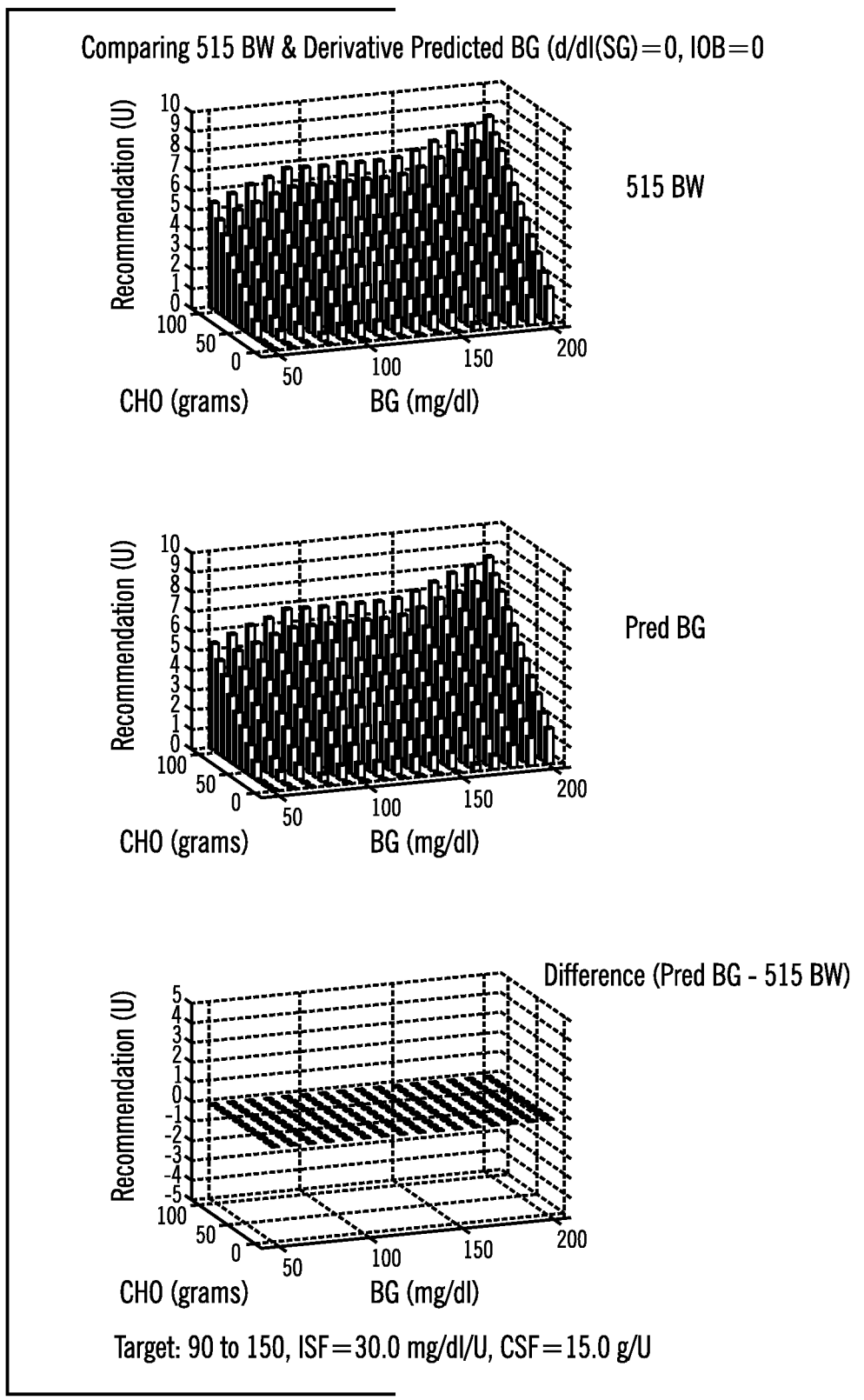
FIG. 1 shows plots of a recommendation envelope of an embodiment of the invention.
Figure 2:
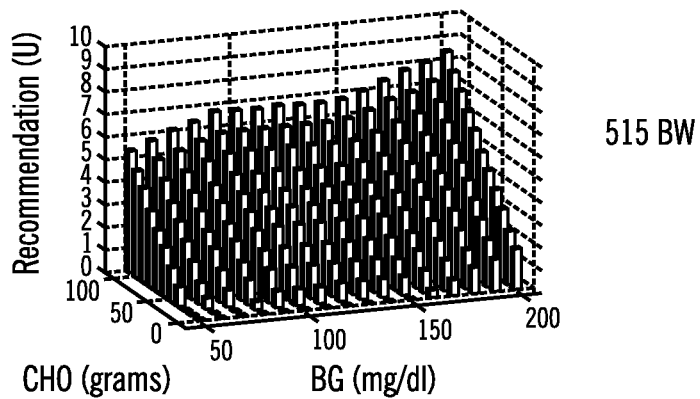
FIG. 2 shows plots of a recommendation envelope of an embodiment of the invention.
Figure 2:
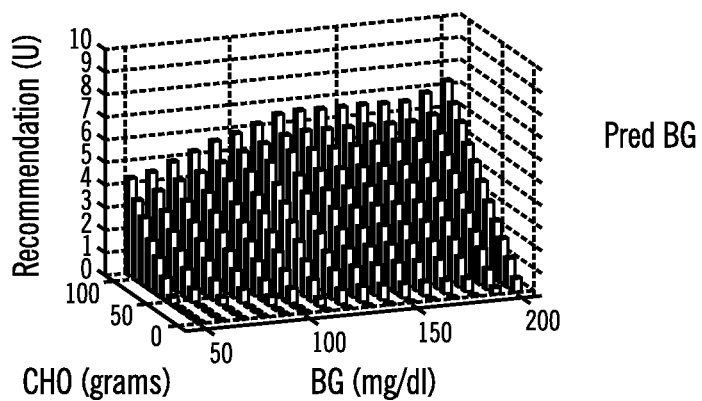
Figure 2:
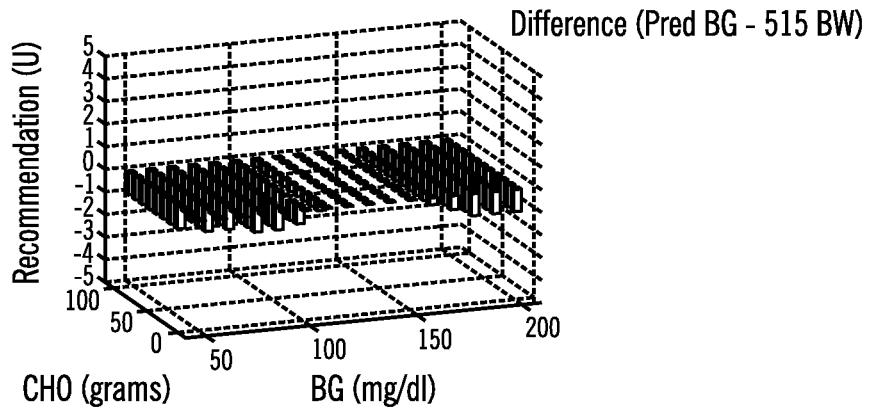
Figure 3:
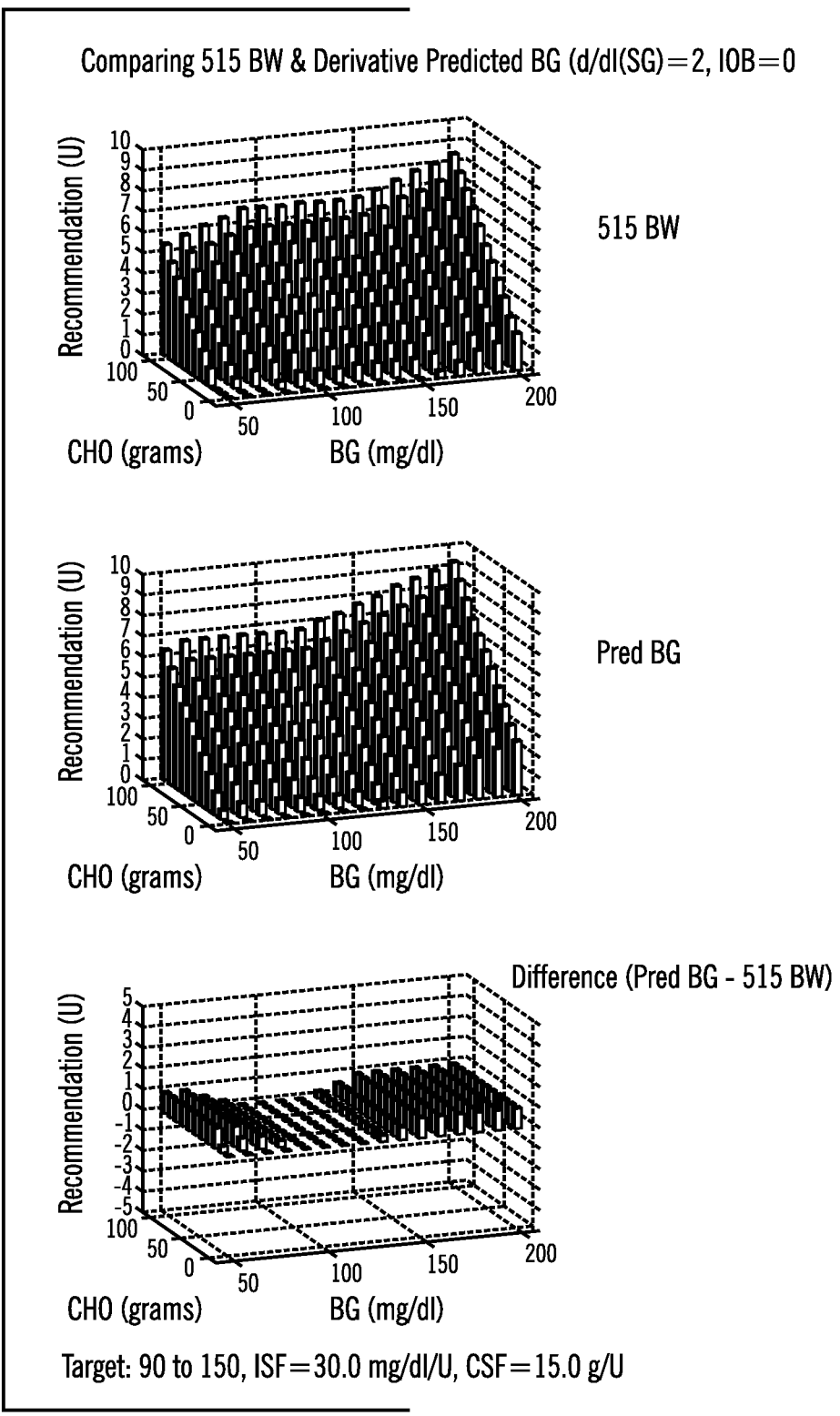
FIG. 3 shows plots of a recommendation envelope of an embodiment of the invention.
Figure 4:
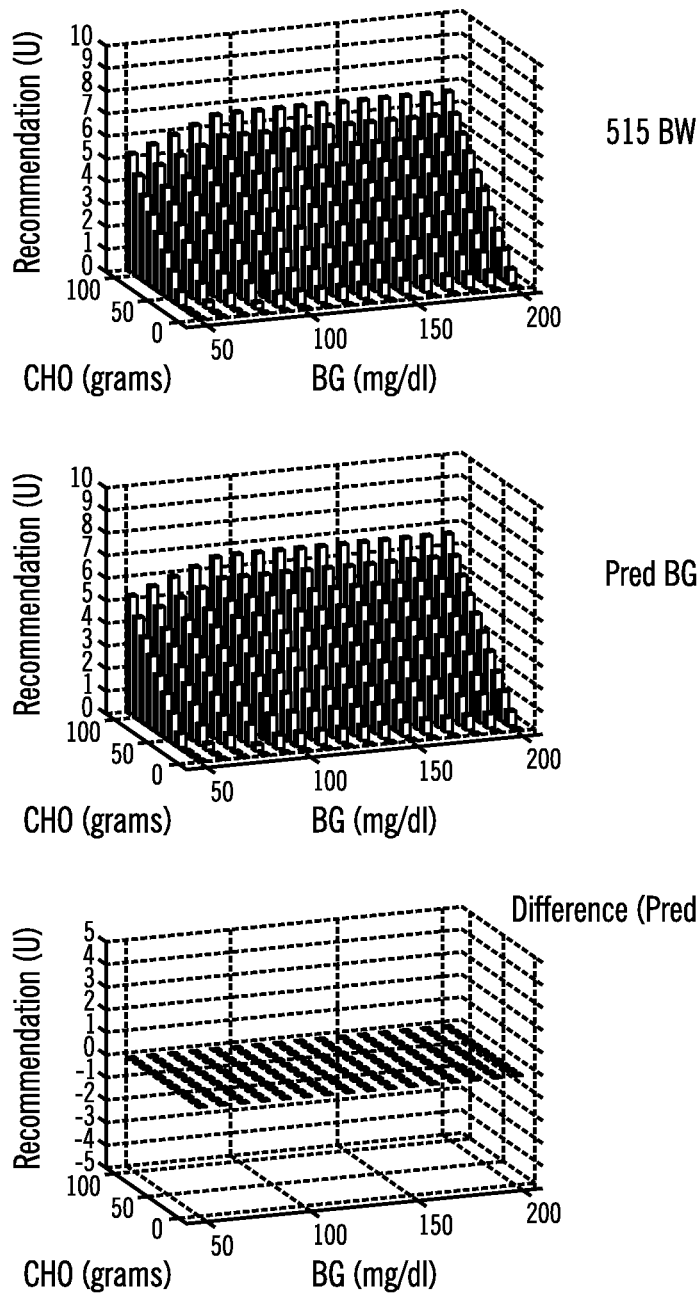
FIG. 4 shows plots of a recommendation envelope of an embodiment of the invention.
Figure 5:
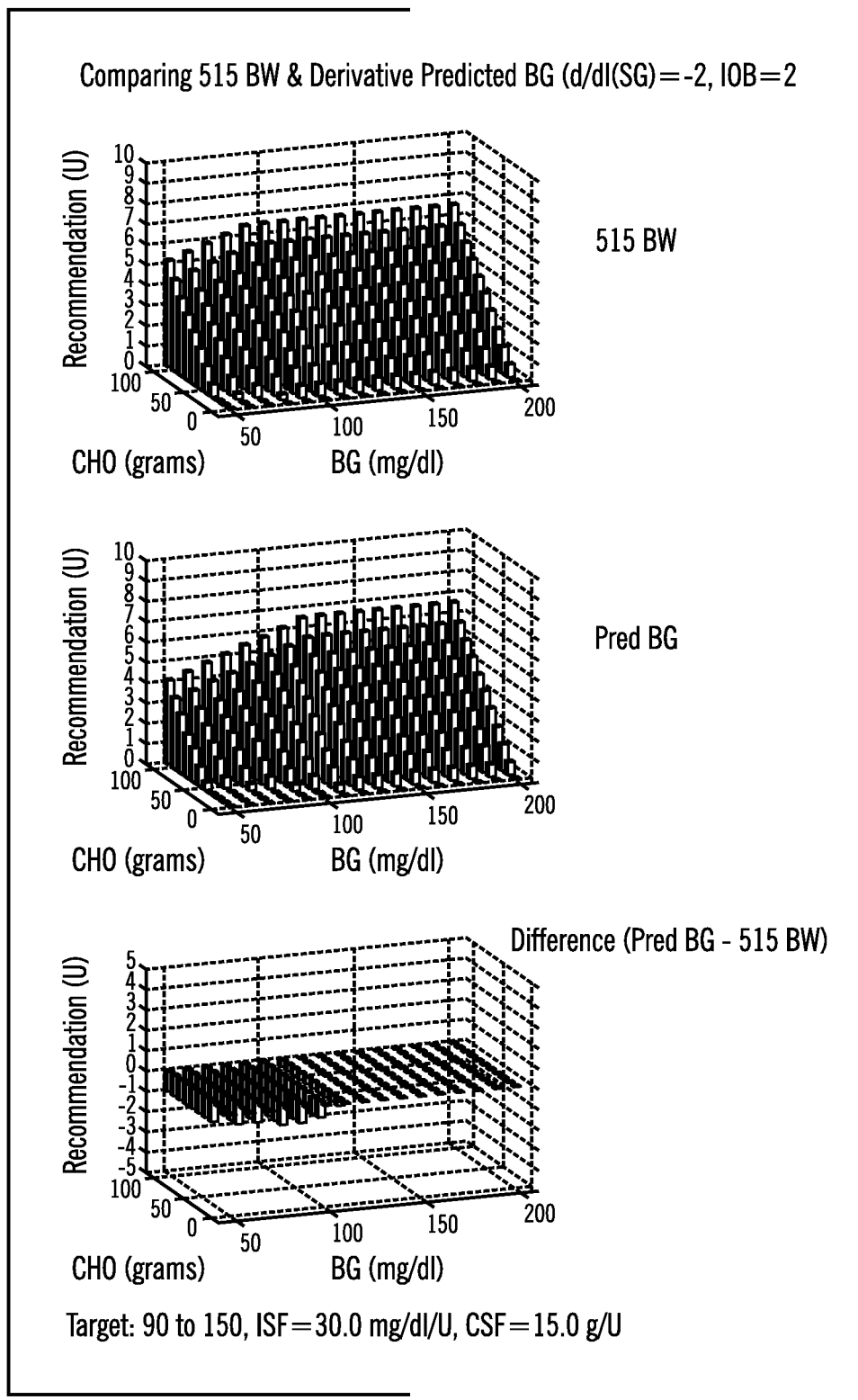
FIG. 5 shows plots of a recommendation envelope of an embodiment of the invention.
Figure 6:
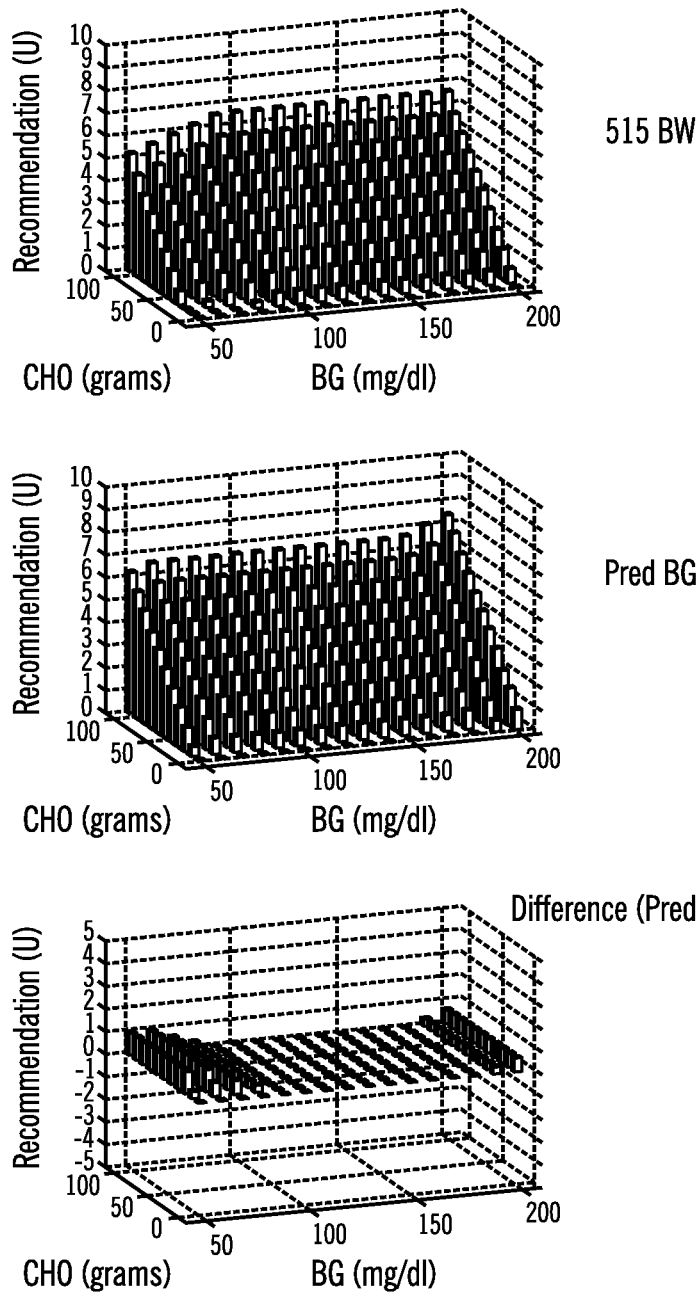
FIG. 6 shows plots of a recommendation envelope of an embodiment of the invention.
Figure 7:
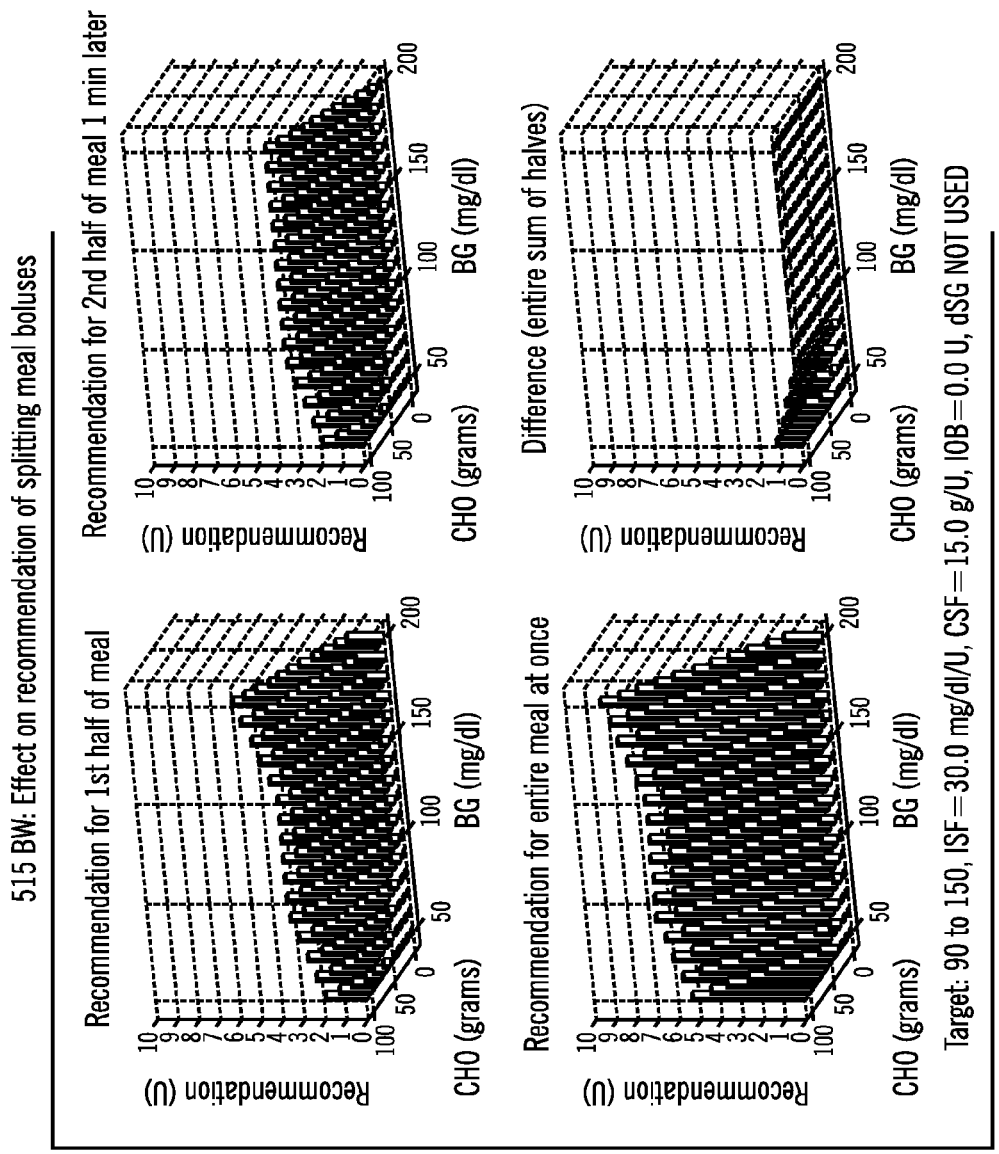
FIG. 7 shows algorithm recommendation envelopes resulting from splitting and not splitting a meal bolus in accordance with traditional infusion devices.
Figure 8:
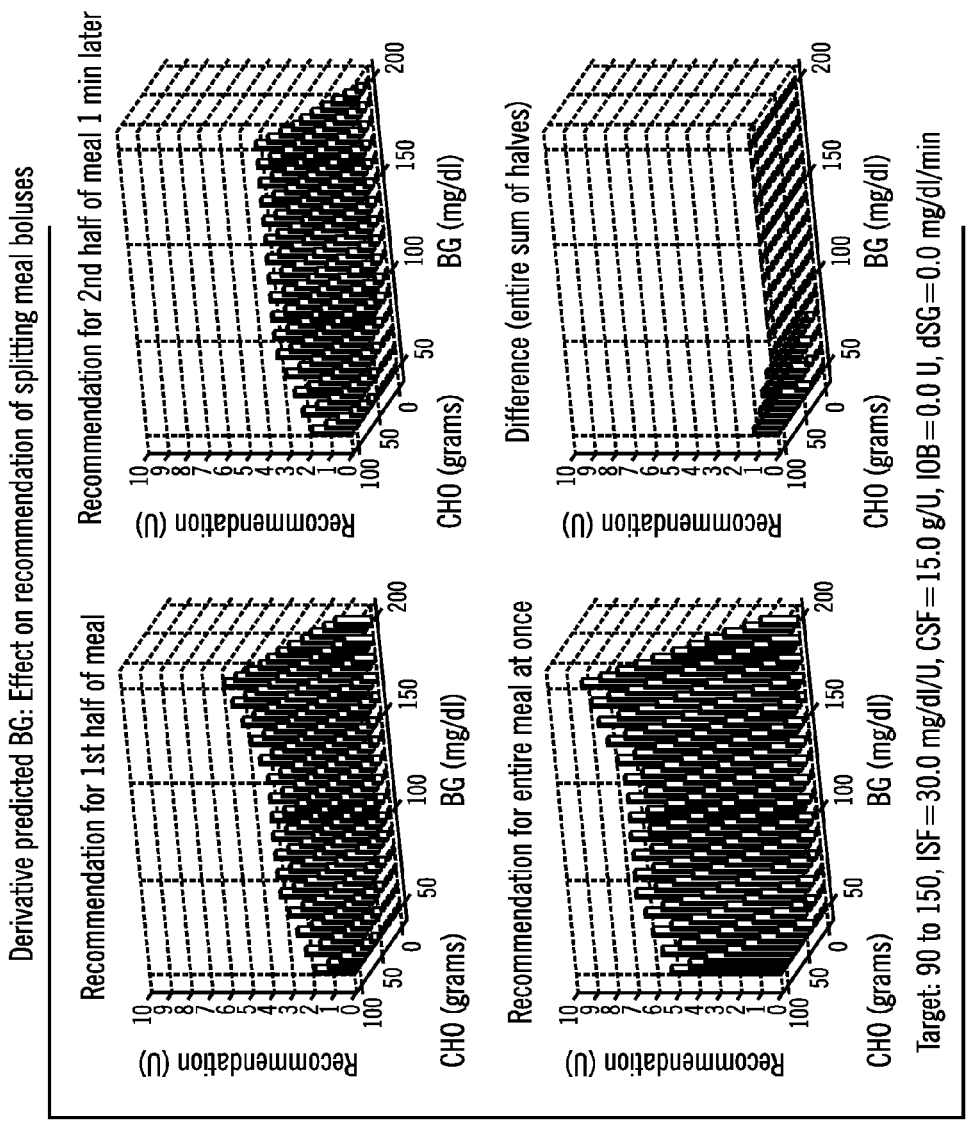
FIG. 8 shows algorithm recommendation envelopes resulting from splitting and not splitting a meal bolus in accordance with an embodiment of the invention.
Figure 9:
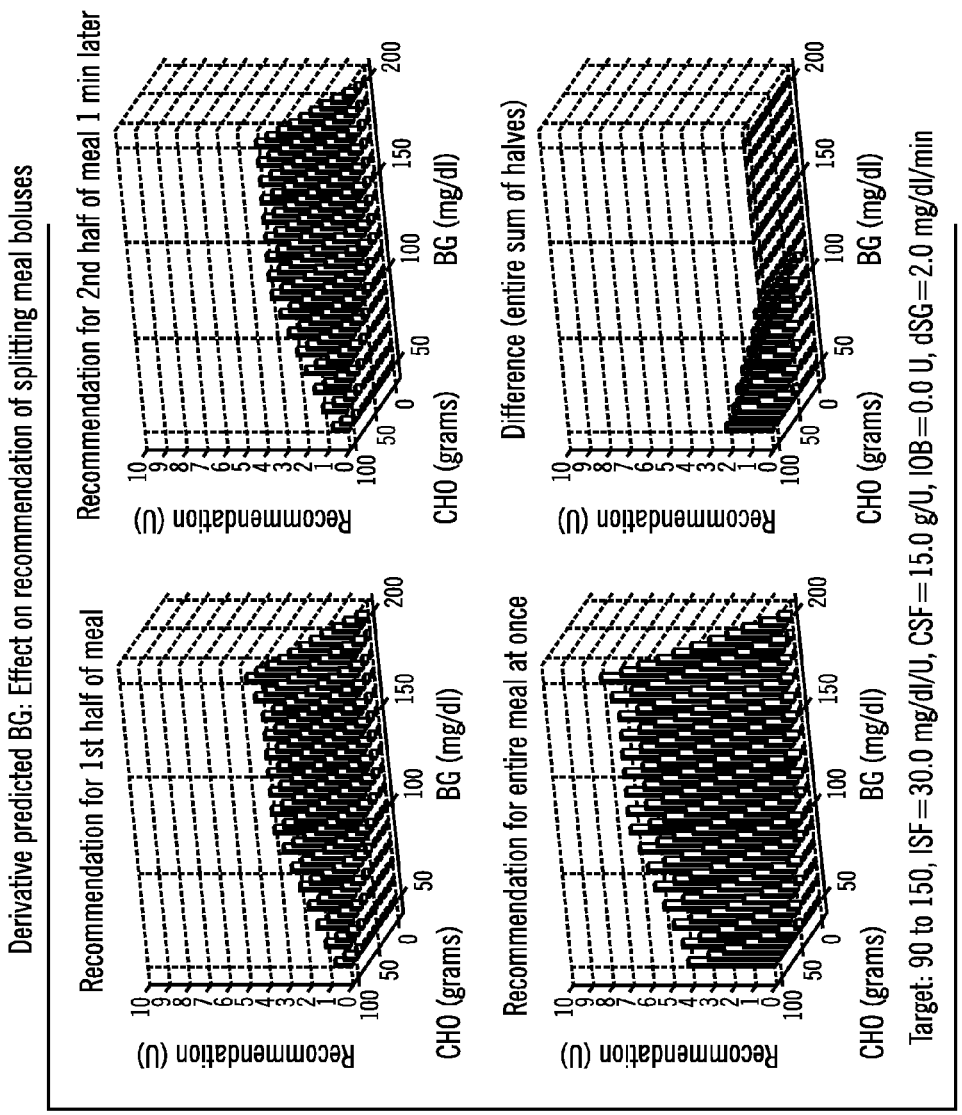
FIG. 9 shows algorithm recommendation envelopes resulting from splitting and not splitting a meal bolus in accordance with an embodiment of the invention.
Figure 10:
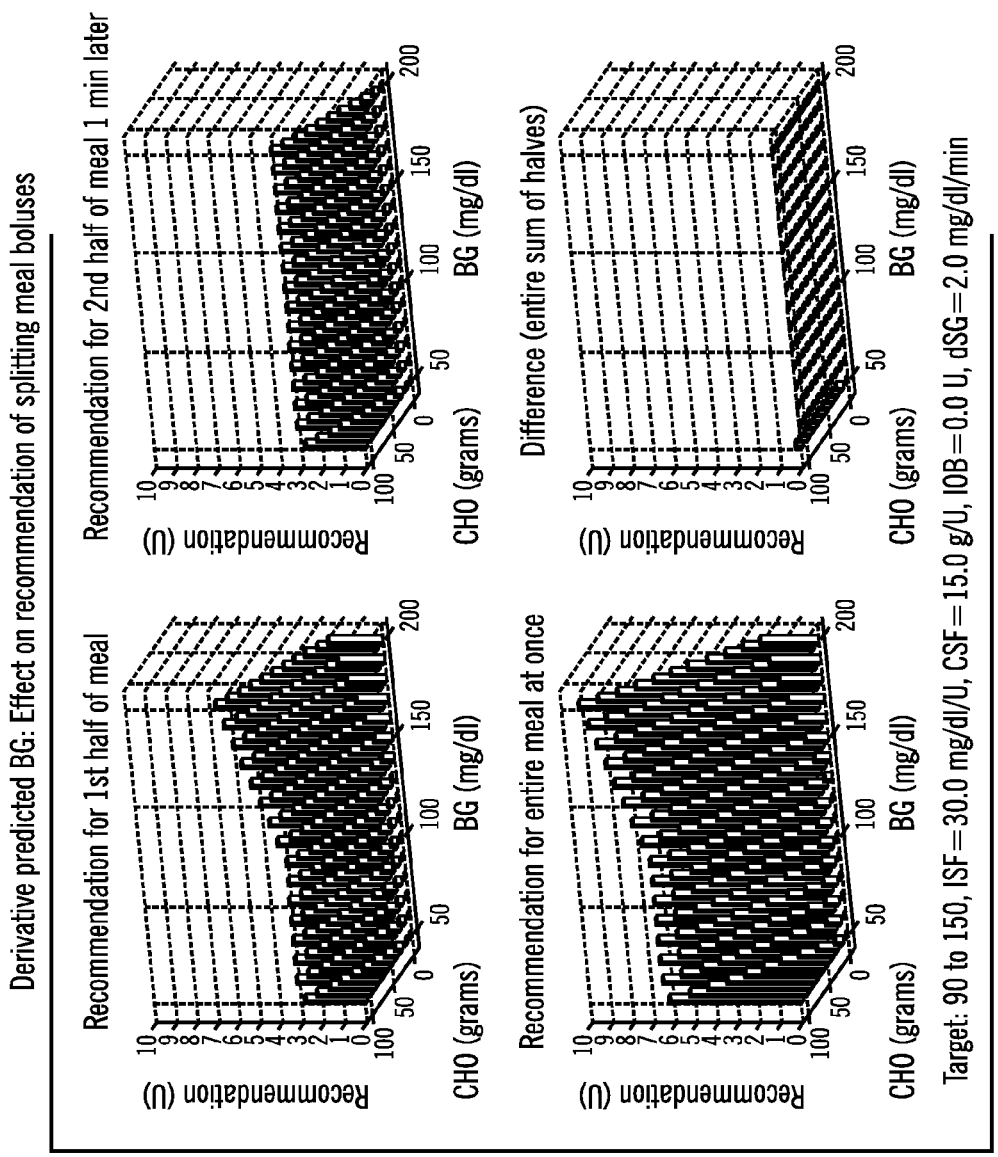
FIG. 10 shows algorithm recommendation envelopes resulting from splitting and not splitting a meal bolus in accordance with an embodiment of the invention.
Figure 11:
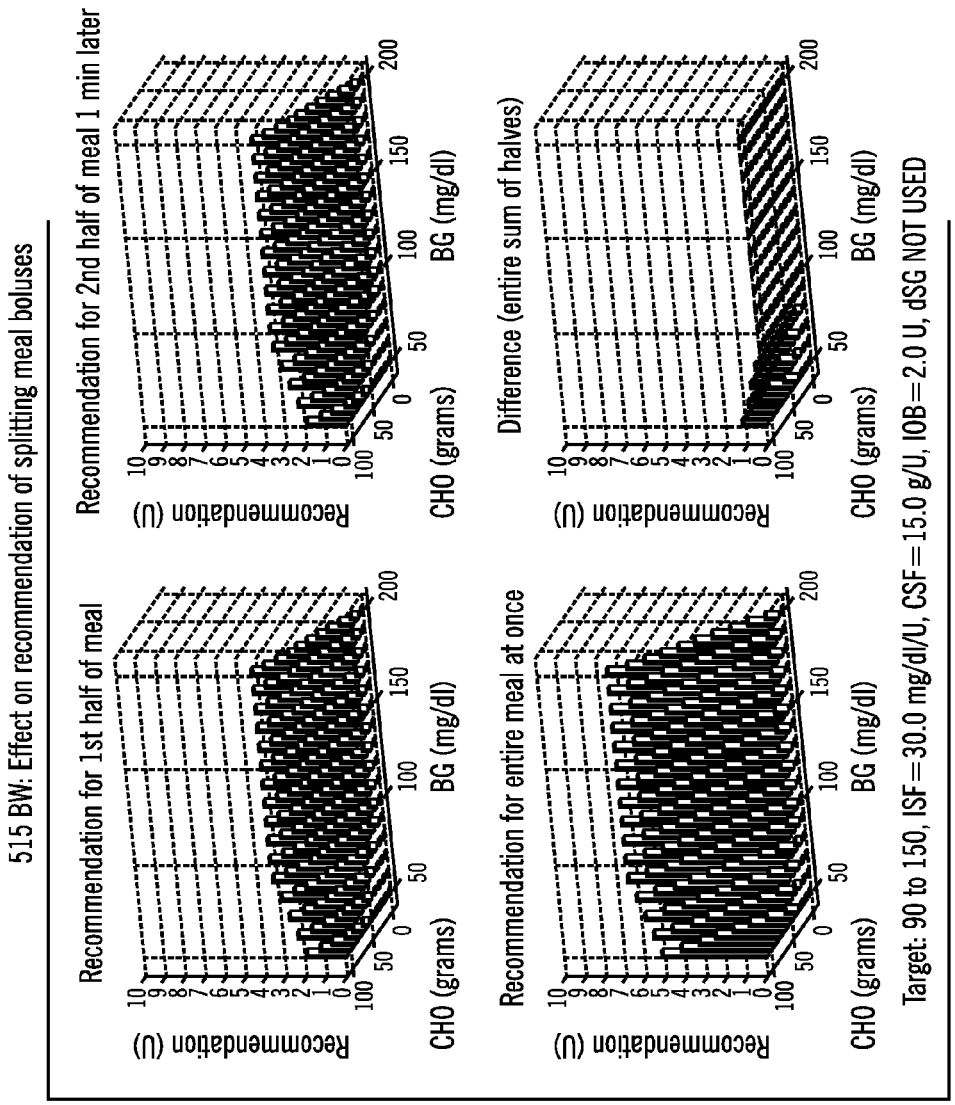
FIG. 11 shows algorithm recommendation envelopes resulting from splitting and not splitting a meal bolus in accordance with traditional infusion devices.
Figure 12:
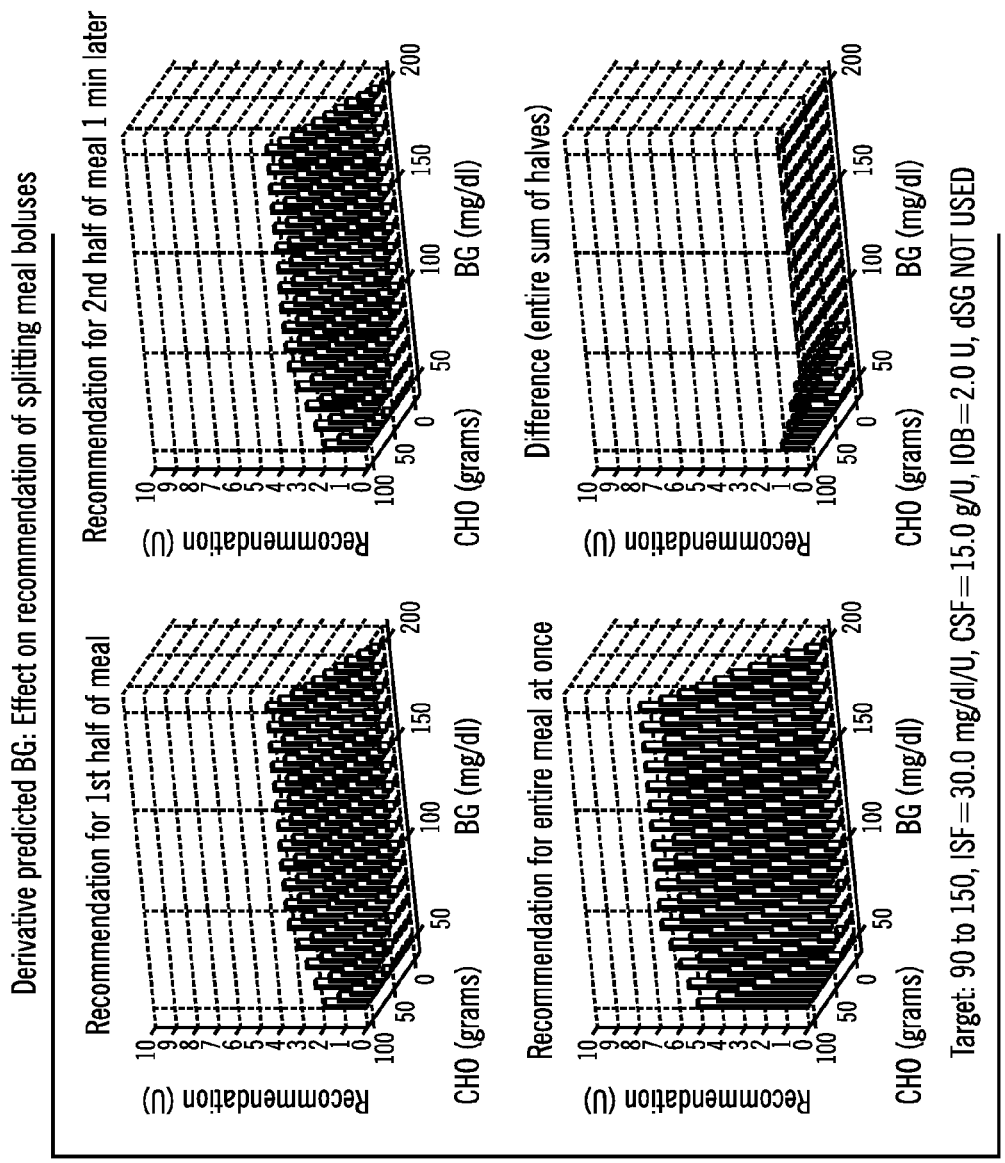
FIG. 12 shows algorithm recommendation envelopes resulting from splitting and not splitting a meal bolus in accordance with an embodiment of the invention.
Figure 13:
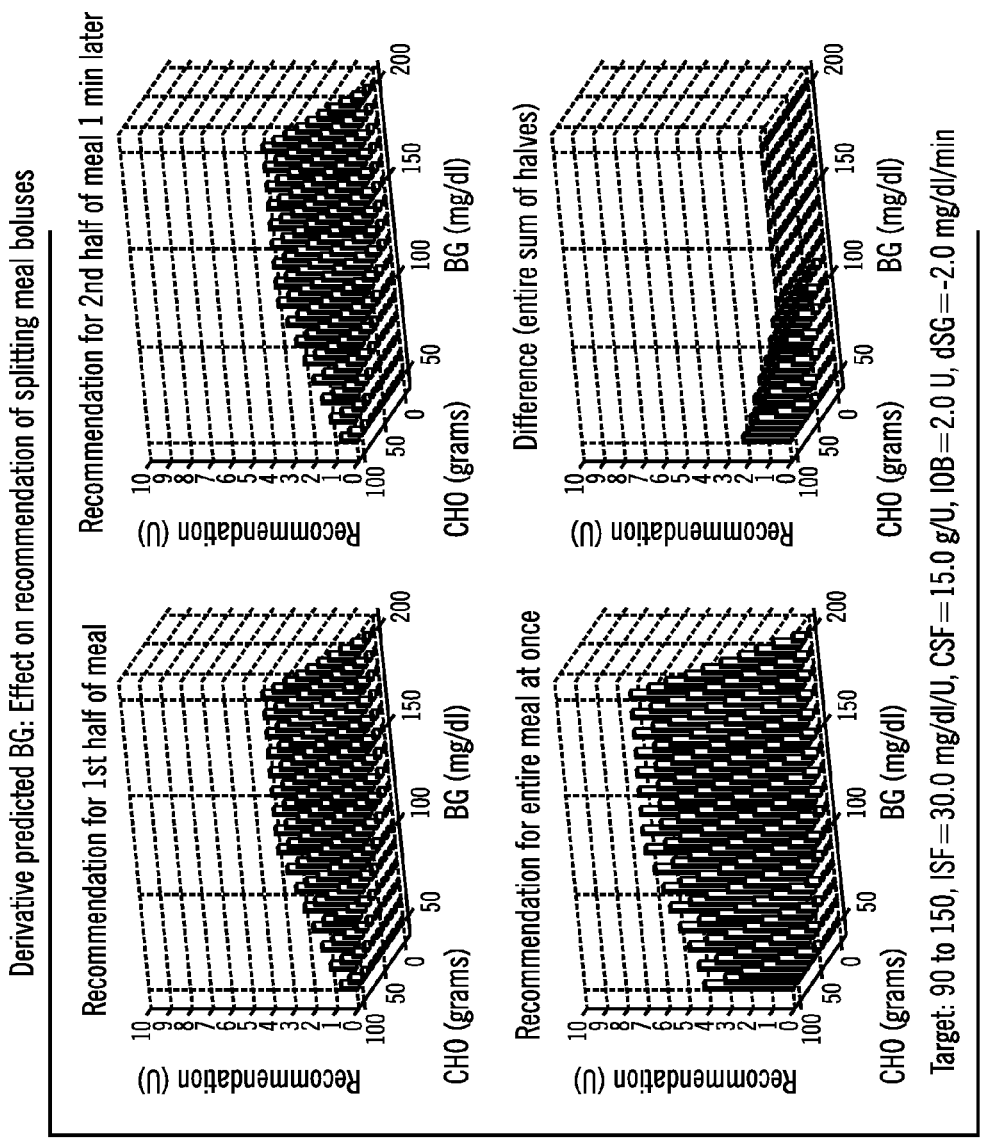
FIG. 13 shows algorithm recommendation envelopes resulting from splitting and not splitting a meal bolus in accordance with an embodiment of the invention.
Figure 14:
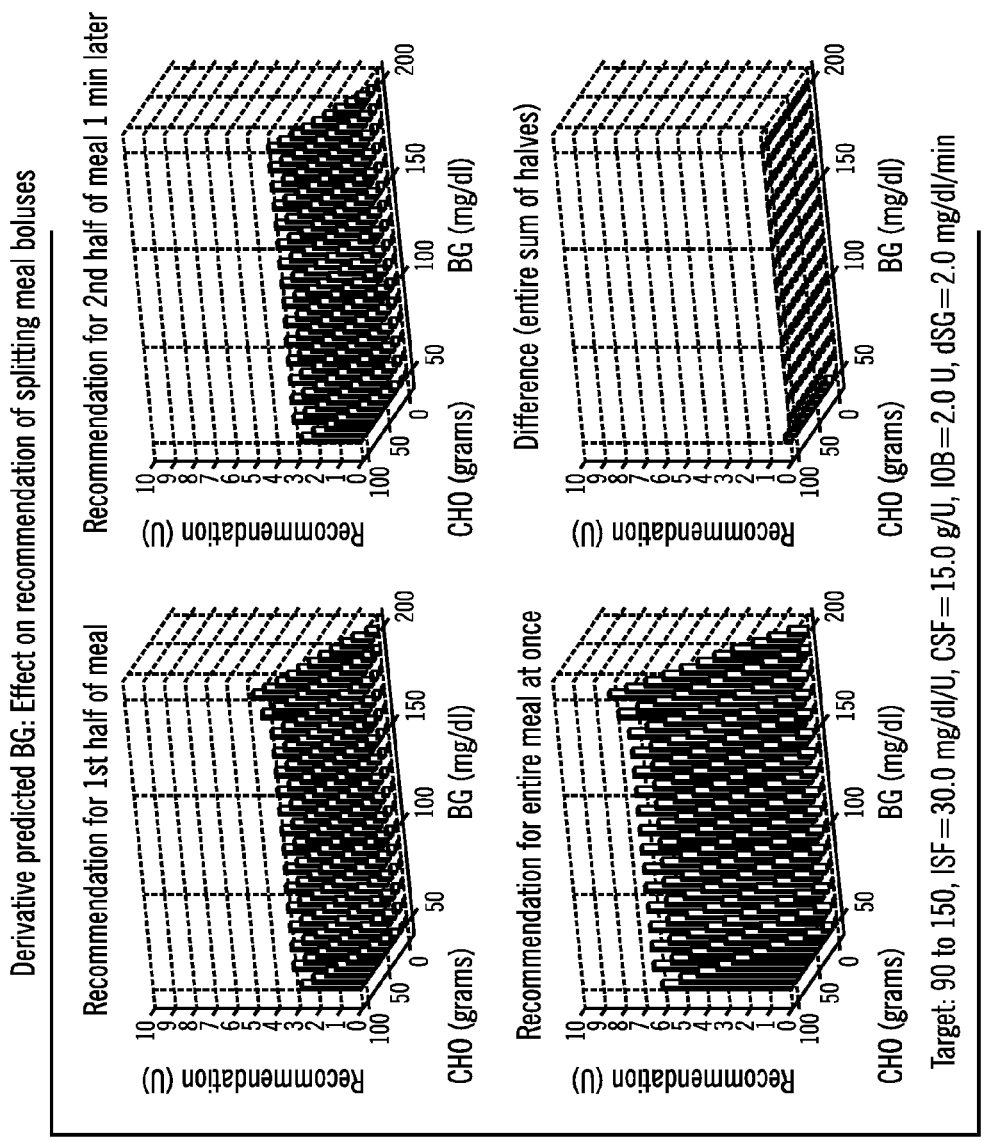
FIG. 14 shows algorithm recommendation envelopes resulting from splitting and not splitting a meal bolus in accordance with an embodiment of the invention.

In some embodiments, temporal discontinuities occur when, for example, the bolus estimator is given the current BG and CHO content of half the meal just ingested, but one minute later (or some other short and/or insignificant amount of time) the estimate is given the current BG (no change) and the CHO content of half the meal ingested one minute ago. In this situation, the sum of the two resulting estimates should equal the estimate yielded when the full CHO content of the meal is provided at once. But in actuality, embodiments of the derivative predicted algorithm may produce different results when splitting the meal bolus versus providing the entire bolus at once. FIGS. 7-14 show recommendation envelopes consisting of four plots. The upper two plots show the recommendation envelope for each half of the split meal bolus. The lower left plot shows the recommendation envelope for the entire meal determined in one estimate. The lower right plot shows the difference at every point on the recommendation envelope (the entire meal at once minus the sum of the split meal boluses). FIGS. 7-10 compare derivative predicted algorithms to traditional infusion device algorithms with IOB equal to 0. FIG. 7 shows plots yielded by an infusion device utilizing traditional algorithms with IOB equal to 0. FIGS. 8-10 show the results of an infusion device utilizing the derivative predicted algorithm discussed above with IOB equal to 0 but with varying values of dSG (0, −2, and +2). FIGS. 11-14 make the same comparisons but with IOB equal to 2 U.

In particular embodiments, when the derivative is positive, the derivative predicted algorithm acts more aggressively, in some embodiments, recommending more insulin than traditional infusion device. In further embodiments, when the derivative is negative, the derivative predicted algorithm may act more conservatively, recommending less insulin than traditional infusion devices. In some embodiments, the derivative predicted algorithm exhibits a split bolus discontinuity in the lower BG range. The effect of the derivative in these embodiments may cause the discontinuity to become more pronounced with negative derivatives and less pronounced with positive derivatives. In some embodiments, the derivative predicted algorithm reacts more quickly to changes in BG, reducing the recommendation sooner for falling BG and increasing it sooner for rising BG, offering improved control of BG.

In particular embodiments, the patient may receive the infusion device pre-programmed with traditional algorithms and/or derivative predicted algorithms. The patient may then decide which algorithm to run based on the patient's grasp of BG control and healthcare provider recommendations. In still additional embodiments, the infusion device may include only the derivative predicted algorithm.

In still further additional embodiments, the derivative predicted algorithm acts more aggressively than traditional correction algorithms employed by current infusion devices. In these embodiments, the derivative predicted algorithm may recommend more insulin when the derivative of SG is positive. However, in other embodiments, when the derivative of SG is negative, the algorithm acts more conservatively, recommending less insulin.

In specific embodiments, the infusion device system may employ various bolus delivery algorithms. In some embodiments, the device may allow the patient to select from three separate delivery algorithms based on patient and/or healthcare professional preference. The first algorithm may utilize traditional methods found in current infusion device systems of the type described in U.S. Pat. No. 6,554,798 entitled "External Infusion Device with Remote Programming, Bolus Estimator and/or Vibration Alarm Capabilities," which is specifically incorporated by reference herein.

The second option allows the patient to utilize the traditional algorithm plus a modification of insulin intake using a glucose trend. This option allows the fine-tuning of the traditional algorithm by examining the trend of sensor derived blood glucose values as described by the algorithms explanation above. In some embodiments, the recommended insulin intake would be less if, in general, BG values were trending down. In other embodiments, the recommended insulin intake would be more if BG values were trending up. In further embodiments, the patient may be required to check the glucose sensor values by administering a finger-stick value. In these instances, SG may not be utilized if it is significantly different from the finger-stick value. In particular embodiments, the difference may be a predetermined range based on percentage in the glucose readings.

The third option allows use of the sensor glucose values to replace the finger stick values in the second option. If a finger stick value was obtained within the last 12 minutes, the algorithm reverts to the second option. If not, the screen of the infusion device will show the present current sensor value. Upon user acknowledgement the bolus estimation will use the sensor value for bolus estimation, effectively replacing the finger stick value in the second option. Finally, the infusion device may display dashes, stars and the like to notify the patient that neither the BG value nor the current sensor value is available to be inputted.

Embodiments of the semi-closed loop infusion system may also provide alarm-based capabilities. In some embodiments, the system performs delivery dosage recommendations autonomously every five minutes. This amount of time may be hard coded into the system so the patient cannot manipulate it; or it may be programmable to change the time between recommendation cycles. Additional embodiments allow the patient to set the amount of time between system recommendations. If the recommendation amounts are within the patient-defined fluid-based thresholds, the system will not display recommended dosages or require the patient to verify that the dosage is sufficient—the processor (controller) will direct the infusion system to deliver the recommended amounts. However, if the recommended delivery amounts exceed or fall below the patient-defined thresholds, the infusion device will provide alarms for too much or too little fluid delivery, followed by displaying the recommendation on the screen for patient input on whether to accept, alter or reject the recommendation. Thus, embodiments of the system allow the processor (controller) to recommend and/or deliver fluids to the body of the patient, without patient interaction, until the recommendation protocol exceeds or falls below patient-defined thresholds. System advantages may include, for example, simulating the body's natural insulin response to blood glucose levels for diabetic patients. For a diabetic patient, input and interaction with an infusion device may only be required when the recommended insulin dosage amount exceeds or falls below predefined thresholds pre-programmed on the device. In the present embodiment, the patient may turn this feature on or off based on the projected usage. In still further embodiments, this feature may be disabled or enabled directly from the factory.

Examples of other reminders provided by the infusion device based on sensor readings and/or trends can be found in U.S. patent application Ser. No. 10/034,139 entitled "System For Monitoring Physiological Characteristics," which is specifically incorporated by reference herein.

In further embodiments, the patient may program multiple sets of high/low thresholds based on time. This feature allows the patient to determine what thresholds may be required for a particular time of day. In the case of diabetic patients, tighter thresholds may be used during nighttime sleep hours to avoid dramatic drops in blood glucose levels. In further embodiments, thresholds may be set for different days of the week, activity levels, meals, health conditions, or the like.

The alarms of the present embodiment include, but are not limited to audible alarms, vibration alarms, visual alarms, and the like. Additional embodiments may include one type of alarm or a combination of various alarms. Further embodiments may allow the patient to configure which type of alarm is used. For example, these embodiments would allow the patient to set a particular type of alarm for an excessive recommendation and a different alarm for a recommendation that falls below the threshold. Alternatively, all alarms may be set the same. The patient may also program the intensity of the alarms. Audible alarms may have the capability to increase and/or decrease in volume, change tones, provide melodies, and the like. Vibration alarms may change in intensity and/or pulse to provide tactile alerts. Visual alarms may come in many forms including, but not limited to, flashing LCD backlights, flashing LEDs, and the like. Examples of alarms are shown in U.S. Pat. No. 6,554,798 entitled "External Infusion Device with Remote Programming, Bolus Estimator and/or Vibration Alarm Capabilities," and U.S. patent application Ser. No. 09/784,949 entitled "Improved Infusion Device Menu Structure and Method of Using the Same," both of which are specifically incorporated by reference herein.

In still further embodiments, the semi-closed loop infusion system can shut-off infusion based on sensor-detected readings and/or sensor-derived trends. For example, in an insulin based infusion system for a diabetic patient, if the sensor detects a low blood glucose level (i.e. hypoglycemia) over a designated period of sensor readings, the infusion device may stop insulin delivery entirely and alert the patient by going into a normal suspend mode. If a low blood glucose level is verified over a period of time, the patient needs to be alerted because it has the potential of causing severe health consequences and continued insulin delivery may make the low blood glucose level worse. Immediate delivery of glucose, not insulin, would be required. In other embodiments, only a portion of insulin delivery may be suspended. In these embodiments, multiple delivery profiles may be activated or suspended based on sensor derived readings, patient input, derivative predicted readings and the like. Activations and suspension of multiple delivery profiles are more fully described in U.S. patent application Ser. No. 10/025,052 entitled "Medication Delivery System and Monitor," which is specifically incorporated by reference herein.

Further embodiments may use predicted sensor readings to determine if low blood glucose levels (i.e. hypoglycemia) will be present a specified amount of time in the future. In these embodiments, sensor-derived trends are utilized to determine low blood glucose levels occurring in the future. The sensor-derived trends may be obtained by utilizing the derivative predicted algorithm described above. The processor (controller) of the infusion device may use current sensor readings to predict sensor readings that will occur a certain amount of time in the future, i.e., fifteen minutes—thus yielding a derivative corrected blood glucose reading. Using this technique, if a predicted sensor-derived blood glucose level falls below a low-shutoff threshold, the infusion device will go into a suspend mode. Similar to the previous embodiment, this suspend mode may provide alerts to the patient. This algorithm may also allow the patient to be aware of predicted low blood glucose levels before they actually occur. The patient will have more time to implement required corrective action. In alternative embodiments, longer times, such as thirty minutes, one hour, several hours, or days, and/or shorter times, such as one minute, five minutes, 10 minutes, or the like may be used with the time set to meet the patient's particular needs and provide safety.

Additionally, in some embodiments, the semi-closed loop infusion system may resume fluid delivery based on sensor-detected readings and/or sensor-derived trends. The infusion device may recommend resumption of insulin delivery based on current sensor readings yielding blood glucose levels that are found in an acceptable range. An alert may be provided to the patient upon determination of these readings. The device may re-start when the patient accepts the recommendation. In additional embodiments, the device's re-start recommendation may be based on sensor-derived blood glucose readings obtained from the processor (controller) utilizing the derivative predicted algorithm. When the sensor-derived trends yield a derivative corrected blood glucose level above the low target of the infusion system's target range, the processor (controller) may recommend resumption of fluid delivery, i.e. basal delivery. In further embodiments, the resumption may occur automatically upon the sensor-detected readings and/or sensor-derived trends reaching certain values determined to meet patient needs and safety. In other embodiments, the device may query the patient to initiate re-start of the device. In still additional embodiments, the sensor-detected readings and/or sensor-derived trends may be uploaded to a remote computer monitored by a healthcare specialist who may then assist the patient in determining if re-start of the device is necessary.

In particular embodiments, the shut-off and resuming capabilities may be based on current sensor readings and/or sensor-derived trends. In other embodiments, the shut-off and resuming capabilities may be based on additional factors including, but not limited to, insulin-on-board, insulin sensitivity, insulin duration factor, and the like. The patient may select to turn off the sensor-derived readings capability and only use the actual sensor data. In other embodiments, the patient may use a combination of sensor readings and sensor-derived trends. In even further embodiments, the infusion device may come pre-programmed with the ability to carry out one or the other, preventing selection by the patient entirely; this would be a lockout feature useful for doctors and/or parents with patients requiring limited access to the system.

In other embodiments, the infusion system may include a safety mechanism in which the system will not allow the patient-defined low target range to be set lower than the system's low shutoff threshold. Additional safety mechanisms may be included in further embodiments including, but not limited to, limitations on the patient-defined threshold amounts, key-guards to prevent inadvertent suspension or activation of the infusion device and the like. Other embodiments include safety limits that set a maximum amount of recommended delivery dosages that can be taken on an hourly basis.

In still further embodiments, the recommended insulin intake options provided by the processor (controller) may use a combination of current sensor readings along with examination of sensor-derived trends. Additional embodiments may include the use of blood glucose meters with in vitro test strip readings to provide more precise recommendations based on current sensor readings. If sensor readings are lost or not properly received by the infusion system, the patient may have the capability to manually enter in current blood glucose levels determined from in vitro test strip measurements. In other embodiments, in vitro test strip measurements may be automatically provided to the infusion device. In still even further embodiments, the infusion system may combine all of the previous elements and allow the patient to determine which combination of elements to base the recommended dosage on. In other embodiments, changes and modifications of the recommendation protocol may only be made by physicians, therapists, or directly from the factory based on specific patient requirements.

Generally, the embodiments of the glucose sensor system include a glucose sensor, sensor electrical components to provide power to the sensor and generate the sensor signal, a sensor communication system to carry the sensor signal to the processor (controller), and a sensor system housing for the electrical components and the sensor communication system.

In additional embodiments, the glucose sensor system is of the type described in U.S. Pat. No. 6,809,653 entitled "Telemetered Characteristic Monitor System And Method Of Using The Same," which is specifically incorporated by reference herein.

Typically, embodiments of the processor (controller) include controller electrical components and software to generate commands for the insulin delivery system based on the sensor signal, and a controller communication system to receive the sensor signal and carry commands to the insulin delivery system. In additional embodiments, the processor (controller) is of the type described in U.S. Pat. No. 6,554,798 entitled "External Infusion Device with Remote Programming, Bolus Estimator and/or Vibration Alarm Capabilities," and U.S. Pat. No. 5,665,065 entitled "Medication Infusion Device With Blood Glucose Data Input," both of which are specifically incorporated by reference herein.

Embodiments of the insulin delivery system include an infusion device and an infusion tube to infuse insulin into the body of the patient. In particular embodiments, the infusion device includes infusion electrical components to activate an infusion motor according to the commands, an infusion communication system to receive the commands from the processor (controller), and an infusion device housing to hold the infusion device as described in U.S. Pat. No. 6,248,093 entitled "Compact Pump Drive System" and U.S. Pat. No. 6,554,798 entitled "External Infusion Device with Remote Programming, Bolus Estimator and/or Vibration Alarm Capabilities," both of which are specifically incorporated by reference herein.

In particular embodiments, the processor (controller) is housed in the infusion device housing and the infusion communication system is an electrical trace or a wire that carries the commands from the processor (controller) to the infusion device. In alternative embodiments, the processor (controller) is housed in the sensor system housing and the sensor communication system is an electrical trace or a wire that carries the sensor signal from the sensor electrical components to the processor (controller) electrical components. In other alternative embodiments, the processor (controller) has its own housing or is included in a supplemental device. In another alternative embodiment, the processor (controller) is located with the infusion device and the sensor system all within one housing. In further alternative embodiments, the sensor, processor (controller), and/or infusion communication systems may utilize a cable, a wire, fiber optic lines, RF, IR, or ultrasonic transmitters and receivers, or the like instead of the electrical traces.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion system for infusing a fluid into the body of a patient, the system comprising:
a sensor system that includes a sensor for monitoring blood glucose concentration of a patient, and produces at least one sensor signal, which is representative of the blood glucose concentration of the patient, and wherein the at least one sensor signal is used to generate at least one sensor signal input;
a controller, wherein the controller uses the at least one sensor signal input and a derivative predicted algorithm to determine at least one sensor-derived blood glucose trend, and wherein the at least one sensor-derived blood glucose trend is used to determine blood glucose levels at a predetermined time in the future, wherein the derivative predicted algorithm calculates a first derivative of a sensor current sample from the at least one sensor signal input at time period n, and then calculates a first derivative of a sensor glucose value from the at least one sensor signal input using the first derivative of the sensor current sample to determine future blood glucose levels, wherein the first derivative of the sensor current sample is calculated from a slope of the sensor current sample versus time using a Savitzky-Golay finite impulse response filter; and
a delivery system that infuses a fluid into the patient, wherein operation of the delivery system is affected by commands from the controller and the patient,
wherein the controller suspends fluid delivery if the at least one sensor-derived trend yields at least one blood glucose level reading that is below a predefined low shutoff threshold.

2. The system according to claim 1, wherein the controller resumes delivery of the fluid when the at least one sensor-derived trend yields at least one blood glucose level reading that is above the predefined low shutoff threshold.

3. The system according to claim 1, wherein the predefined low shutoff threshold is always above the infusion system's lowest shutoff threshold.

4. The system according to claim 1, wherein the infused fluid is insulin.

5. The system according to claim 1, wherein the infusion system further includes an alarm to provide alerts to the patient.

6. The system according to claim 1, wherein the patient selects at least one alarm to activate, wherein the at least one alarm includes an audible alarm for providing audible alerts, a vibration alarm for providing tactile alert, and a visual alarm for providing visual alerts.

7. The system according to claim 1, wherein the controller recommends more fluid delivery based on a positive derivative from the derivative predicted algorithm, and the controller recommends less fluid delivery based on a negative derivative from the derivative predicted algorithm.

8. The system according to claim 1, wherein the controller commands the delivery system to deliver fluid to the patient when future blood glucose levels are in the patient's predefined target range.

* * * * *